United States Patent [19]

Innes et al.

[11] 4,045,373

[45] Aug. 30, 1977

[54] OXIDATION CATALYSTS AND PROCESS FOR PREPARING SAME

[75] Inventors: Robert A. Innes, Pittsburgh; Anthony J. Perrotta, Monroeville, both of Pa.

[73] Assignee: Gulf Research & Development Company, Pittsburgh, Pa.

[21] Appl. No.: 645,418

[22] Filed: Dec. 30, 1975

[51] Int. Cl.$^2$ .................... B01J 23/14; B01J 23/16
[52] U.S. Cl. ................... 252/469; 260/465.3; 260/604 R; 423/593
[58] Field of Search ............ 252/469; 260/465.3, 260/604 R; 423/593

[56] References Cited

U.S. PATENT DOCUMENTS

| 3,408,400 | 10/1968 | Bohemen et al. ............... 260/604 R |
| 3,769,241 | 10/1973 | Stewart et al. ............... 252/469 |

FOREIGN PATENT DOCUMENTS

| 11,927 | 7/1967 | Japan ............... 260/465.3 |

*Primary Examiner* — W. J. Shine

[57] ABSTRACT

Novel compounds particularly suitable as oxidation catalysts are prepared using critical amounts of uranium, antimony and tin.

5 Claims, No Drawings

OXIDATION CATALYSTS AND PROCESS FOR PREPARING SAME

BACKGROUND OF THE INVENTION

1. Field of the Invention

This invention is directed to novel compounds particularly suitable as oxidation catalysts containing critical amounts of uranium, antimony and tin and to a procedure for preparing the same using critical amounts of said elements.

2. Description of the Prior Art

Oxidation catalysts consisting essentially of oxides of antimony and uranium are old and well known. Such catalysts and their uses are described in U.S. Pat. Nos. 3,198,750 and 3,308,151 to Callahan and Gertisser. Antimony-uranium oxide catalysts are used primarily for converting propylene, in the presence of ammonia and a gas containing molecular oxygen, to acrylonitrile. Other uses include the ammoxidation of isobutylene to methacrylonitrile and the oxidative conversions of propylene to acrelein, isobutylene to methacrolein, butene-1 or butene-2 to 1,3-butadiene, and isoamylenes to isoprene. It has been shown by Grasselli and Callahan in the *Journal of Catalysis*, 14, 93–103 (1969) that the most effective catalysts are obtained when the antimony to uranium atomic ratio is greater than three. Their best catalyst had an antimony to uranium atomic ratio of 4.6. The sole uranium containing phase detected in this catalyst was $USb_3O_{10}$ according to Grasselli and Suresh, *Journal of Catalysis*, 25, 273–291 (1972). The excess antimony oxide insured that undesirable uranium containing phases such as $USbO_5$ and $U_3O_8$ were not formed. U.S. Pat. No. 3,816,596 to Wise describes a method of making a catalyst consisting essentially of $USb_3O_{10}$. Antimony-uranium oxide catalysts may be made attrition resistant by adding silica as described in U.S. Pat. No. 3,341,471 to Callahan et al.

Attempts have been made to improve the antimony-uranium oxide catalyst by combining the optimum antimony-uranium oxide composition with the oxides of most of the metallic elements of the Periodic Table. See, for example, U.S. Pat. Nos. 3,328,315 and 3,431,292 to Callahan et al and British Pat. No. 1,007,929 to Distiller's Company Limited. Based on starting materials, every catalyst tested in these patents had an antimony to uranium atomic ratio of 4.0 or 4.6, i.e. close to the optimum composition of Grasselli and Callahan.

SUMMARY OF THE INVENTION

We have found that if we heat for a sufficient length of time at a temperature of at least about 800° C. an intimate mixture containing (1) oxides of uranium, antimony and tin or (2) compounds of said elements that will decompose or will otherwise be converted to said oxides at said temperature, wherein the atomic ratios of said elements are within selected critical ranges, preferably in molecular oxygen, such as air, we obtain a catalyst in which said elements and oxygen are present within selected critical atomic ratios which catalyst is more highly active as an oxidation catalyst than the prior art catalysts referred to above and which exhibits excellent selectivity in the production of acrylonitrile from propylene.

Examples of oxides that may be heated as part of the mixture described above include $UO_2$, $U_3O_8$, $UO_3$, $Sb_2O_3$, $Sb_2O_4$, $Sb_2O_5$, $SnO_2$, $SnO$, $USbO_5$, $USb_3O_{10}$. Examples of compounds that will be converted to these oxides upon heating include $UO_2(NO_3)_2.6H_2O$, $UO_2C_2O_4.3H_2O$, $UO_2(C_2H_3O_2)_2.2H_2O$, $Sb_2(C_4H_4O_6)_3.6H_2O$, $Sb(C_2H_3O_2)_3$, $Sn(NO_3)_4$, $SnC_2O_4$, $SnC_4H_4O_6$, and any hydrated oxide or hydroxide of antimony, uranium, or tin.

Intimate mixing of the above materials greatly facilitates the formation of the desired catalyst. In a preferred embodiment of our invention, intimate mixing is achieved by coprecipitation of the hydroxides or hydrated oxides from acidic solution by adding a suitable base such as ammonium hydroxide. The precipitate so obtained is washed with water, dried at a temperature of 100°–200° C. for from two to 24 hours and then calcined. The acidic solution is conveniently prepared using various soluble salts as starting materials. These include $UO_2(NO_3)_2.6H_2O$, $UO_2(C_2H_3O_2)_2.2H_2O$, $UCl_3$, $UCl_4$, $UF_6$, $UBr_4$, $SbCl_3$, $Sb(C_2H_3O_2)_3$, $SbF_3$, $SbCl_5$, $SnCl_4$ and $SnCl_2.2H_2O$.

Alternatively, one can prepare acidic solutions from the metals themselves or their oxides. For example Sb metal can be reacted with concentrated nitric acid to obtain the hydrous oxide, which can be dissolved in concentrated hydrochloric acid.

The amounts of the reactant components used in the preparation of the catalyst herein are critical. Thus the metals in the reactant components must be present in amounts such that the atomic ratio of antimony to uranium is at least about 1.35:1, preferably at least about 1.50:1, but no higher than about 2.75:1, preferably no higher than about 2.5:1, the atomic ratio of tin to uranium is at least about 0.25:1, preferably at least about 0.5:1, but no higher than about 1.65:1, preferably no higher than about 1.5:1. In addition the atomic ratios of the sum of antimony and tin to uranium must be within a range of about 3.5:1 to about 2.5:1, preferably about 3.3:1 to about 2.7:1. We have found that such reactant amounts are critical if we are to obtain the new catalysts herein having critical amounts of uranium, antimony, tin and oxygen falling within the following stoichiometric amounts:

$USb_aSn_bO_{8-12}$, wherein a is the number about 2.75 to about 1.35, preferably about 1.5 to about 2.5, and b is the number about 0.25 to about 1.65, preferably about 0.5 to about 1.5. In addition the atomic ratios of the sum a and b must be within the range of about 2.5 to about 3.5, preferably about 2.7 to about 3.3. If amounts outside the reactant amounts are used in the attempted preparation of the new catalysts, the new catalysts defined above are not obtained. In such latter case the catalysts so obtained will not have the increased activity and the good selectivity of the novel catalysts whose stoichiometry is defined above.

Once the critical amounts of reactant components are selected, the reaction mixture containing the same must be heated (calcined) to a critical temperature of at least about 800° C., preferably at least about 875° C., preferably in an atmosphere containing molecular oxygen in order to obtain the defined novel catalyst. Although the temperature can be as high as about 1050° C., or even higher, in general a temperature of about 1000° need not be exceeded. Once having selected a critical temperature within the above range, the mixture is maintained at such temperature for a time sufficient to obtain the novel catalysts having the defined stoichiometric ratios. At the lower temperatures, longer calcination periods are required, while at the higher temperatures lower periods will suffice. Thus, the time required for calcination can be as low as about 15 minutes, generally at least about one hour, but a period of no more than about 24 hours, generally no more than about 18 hours, will suffice. The heating is carried out at atmospheric pressure, although elevated pressures can be used if desired.

The catalyst obtained herein can be employed as an oxidation catalyst using conventional procedures. Thus, in the conversion of propylene to acrylonitrile, in the presence of ammonia and a gas containing molecular oxygen, such as air or oxygen itself, a gaseous mixture containing such reactants is brought into contact with the novel catalyst defined herein at a pressure of about 0 to about 100 pounds per square inch gauge (about 0 to about 7.0 kilograms per square centimeter), preferably about 0 to about 50 pounds per square inch gauge (about 0 to about 3.5 kilograms per square centimeter), in a temperature range of about 375° to about 525° C., preferably about 450° to about 495° C., at a contact time of at least about 0.01 second, preferably in the range of about 0.1 to about 15 seconds. The molar ratio of oxygen to propylene is about 0.5:1 to about 5:1, preferably about 1:1 to about 2:1, while the molar ratio of ammonia to propylene is greater than about 0.9:1 but preferably no greater than about 1.5:1. By contact time we mean the bulk volume of the catalyst in cubic centimeters divided by the flow rate of the total reactants in vapor form at reaction conditions in cubic centimeters per second. The novel catalyst herein can be used in a fixed-bed or a fluidized-bed reactor.

DESCRIPTION OF PREFERRED EMBODIMENTS

The following will provide a further understanding of the invention claimed herein.

EXAMPLE I

To a solution containing 91.24 grams of $SbCl_3$ and 1000 cc. of distilled water there was first added 400 cc. of concentrated HCl and then a solution containing 100.42 grams of $UO_2(NO_3)_2.6H_2O$ and 1000 cc. of distilled water. To the resulting solution there was added a solution containing 70.12 grams of $SnCl_4.5H_2O$ in 1000 cc. of distilled water. The hydrous metal oxides were precipitated from solution by the addition thereto of 1200 cc. of concentrated ammonium hydroxide. The precipitate obtained was filtered, washed with 16 liters of distilled water and then placed in a drying oven for about 16 hours at a temperature of about 120° C. The dried precipitate was then calcined in air at a temperature of 910° C. for 16 hours. In this example, as well as those following, the preparation was carried out at atmospheric pressure and atmospheric temperature. The product obtained had the following stoichiometry: $USb_2SnO_{9.10}$. This product falls within the definition of the novel catalyst herein.

EXAMPLE II

Example I was repeated except that the following amounts of reactants were used: 35.06 grams of $SnCl_4.5H_2O$ in 4000 cc. of distilled water, 104.9 grams of $SbCl_3$ in 1000 cc. of distilled water and 50.21 grams of $UO_2(NO_3)_2.6H_2O$ in 1000 cc. of distilled water. The catalyst obtained possessed the following stoichiometry: $USb_{4.6}SnO_x$. This product does not fall within the definition of the novel catalyst herein.

EXAMPLE III

Example I was repeated, this time with the following amounts of reactants: 7.36 grams of $SnCl_4.5H_2O$ in 1000 cc. of distilled water, 104.9 grams of $SbCl_3$ in 1000 cc. of distilled water and 50.2 grams of $UO_2(NO_3)_2.6H_2O$ in 1000 cc. of distilled water. The product obtained possessed the following stoichiometry: $USb_{4.6}Sn_{0.21}O_x$. This product does not fall within the definition of the novel catalyst herein.

EXAMPLE IV

To a solution containing 100 cc. of water and 6.84 grams of $SbCl_3$ there was first added 40 cc. of concentrated HCl and then a solution containing 100 cc. of water and 5.02 grams of $UO_2(NO_3)_2.6H_2O$. The hydrous metal oxides were precipitated from solution by the addition thereto of 120 cc. of concentrated ammonium hydroxide. The precipitate obtained was filtered, washed with one liter of water and then placed in a drying oven for about 16 hours at a temperature of 120° C. The dried precipitate was then calcined in air at a temperature of 910° C. for 16 hours. In this example, as well as in those following, the preparation was carried out at atmospheric pressure and, unless otherwise stated, at atmospheric temperature. The product obtained, amounting to 7.05 grams, was shown by X-ray diffraction patterns to be the crystalline chemical compound $USb_3O_{10}$, with only small amounts (less than about 10 weight percent, based on the total compounds produced) of $Sb_2O_4$ and $USbO_5$.

Each of the above catalysts was used to prepare acrylonitrile as follows. A 0.5 ml. sample of 20–40 mesh catalyst was weighed and charged to a 0.64 cm. O.D. × 0.48 cm I.D. tubular stainless-steel microreactor. The reactor was placed in an electric furnace. Air was flowed over the catalyst at the rate of 32.5 cc.-STP min$^{-1}$ as the furnace was heated to about 450° C. When the furnace temperature reached 450° C., the reaction was carried out in cyclic fashion. The ammonia and propylene flows were started at 3.0 and 2.5 cc-STP min$^{-1}$, respectively. The furnace temperature was adjusted so that the reaction temperature as measured by a sheathed thermocouple located within the catalyst bed was 475° C. After 15 minutes on-stream, the product stream was sampled and then analyzed by gas chromatography. After another 15 minutes on-stream, the propylene and ammonia flows were shut off. The catalyst was regenerated by allowing the air flow to continue for 30 minutes. Propylene and ammonia flows were then resumed to begin the next on-stream period. This procedure was repeated for five or six cycles.

Thus propylene, air and ammonia were reacted at atmospheric pressure in a 1.0:13:1.2 molar ratio at a contact time of 0.28 to 0.29 second.

Average values are reported in Table I for percent conversion, percent selectivity, percent yield, and relative activity. These are defined as:

$$\text{Percent Conversion} = \frac{\text{moles of propylene converted}}{\text{moles of propylene fed}} \times 100$$

$$\text{Percent Selectivity} = \frac{\text{moles of acrylonitrile produced}}{\text{moles of propylene reacted}} \times 100$$

$$\text{Percent Yield} = \frac{\text{moles of acrylonitrile produced}}{\text{moles of propylene fed}} \times 100$$

$$\text{Relative Activity} = \frac{\text{Ln}(1-X)^{-1}}{(0.3594)(\text{wt. of catalyst})}$$

where X is the mole fraction of propylene converted.

TABLE I

| Run No. | Catalyst From Example | Stoichiometry | | | Grams of Catalyst | Mol Per Cent Propylene Converted | Per Cent Selectivity To Acrylonitrile | Acrylonitrile Yield | Relative Activity |
| --- | --- | --- | --- | --- | --- | --- | --- | --- | --- |
|  |  | U | Sb | Sn |  |  |  |  |  |
| 1 | I | 1.0 | 2.0 | 1.0 | 0.639 | 95.0 | 82.0 | 77.9 | 13.0 |
| 2 | II | 1.0 | 4.6 | 1.0 | 0.531 | 19.8 | 82.5 | 16.3 | 1.2 |
| 3 | III | 1.0 | 4.6 | 0.21 | 0.847 | 38.2 | 82.8 | 31.6 | 1.6 |
| 4 | IV | 1.0 | 3.0 | 0 | 0.495 | 16.3 | 80.3 | 13.1 | 1.0 |

The data in Table I amply emphasize the uniqueness of the novel catalyst herein. Note that when a catalyst was employed in Run No. 1 that fell within the definition of the novel catalyst herein for converting propylene, ammonia and air to acrylonitrile, 95 percent of the propylene was converted, the yield to desired acrylonitrile was 77.9 percent and its relative activity was 13.0. When catalysts outside the definition were used in Examples 2 and 3 conversions, acrylonitrile yields and relative activity were low. While the relative activity of the novel catalyst herein was 13.0, note that the relative activity in Runs Nos. 2 and 3, was only 1.2 and 1.6, respectively. When the base catalyst containing only uranium and antimony was used in Run No. 4, the acrylonitrile yield was only 13.1 percent and its activity was 1.0.

The novel catalyst of this invention can be combined with a binder or support, such as silica, in any conventional manner to make the catalyst attrition resistant so that it can be used in a fluidized bed reactor.

Although the novel catalyst herein has been shown to be very effective in the ammoxidation of propylene to acrylonitrile, the catalyst can also be used advantageously in other ammoxidation reactions such as the ammoxidation of isobutylene to methaacrylonitrile, and in oxidation reactions, such as oxidation reactions converting propylene to acrolein, isobutylene to methacrolein, butene-1 or butene-2 to 1,3-butadiene, and isoamylenes to isoprene.

Obviously, many modifications and variations of the invention, as hereinabove set forth, can be made without departing from the spirit and scope thereof, and, therefore, only such limitations should be imposed as are indicated in the appended claims.

We claim:

1. A novel catalyst defined by the following stoichiometry: $USb_aSn_bO_{8-12}$, wherein a is the number about 2.5 to about 1.5 and b is the number about 0.5 to about 1.5, with the atomic ratio of the sum of antimony and tin to uranium being about 2.5:1 to about 3.5:1.

2. A process for preparing a compound containing uranium, antimony and tin which comprises heating (1) oxides of uranium, antimony and tin, or (2) compounds of said elements that will decompose or be converted to said oxides during said heating, wherein the atomic ratio of antimony to uranium is about 2.5:1 to about 1.5:1, the atomic ratio of tin to uranium is about 0.5:1 to about 1.5:1 and the atomic ratio of the sum of antimony and tin to uranium is about 3.5:1 to about 2.5:1, in an atmosphere containing molecular oxygen at a temperature of at least about 800° C. for about 15 minutes to about 24 hours.

3. The process of claim 2 wherein the atomic ratio of antimony to uranium is about 1.5:1 to about 2.5:1, the atomic ratio of tin to uranium is about 0.5:1 to about 1.5:1 and the atomic ratio of the sum of antimony and tin to uranium is about 3.3:1 to about 2.7:1.

4. The process of claim 2 wherein the temperature is about 875° to about 1000° C. and the time about one to about 18 hours.

5. The catalyst of claim 1 wherein the atomic ratio of the sum of antimony and tin to uranium is about 2.7:1 to about 3.3:1.

* * * * *